US010327685B2

(12) United States Patent
Keith et al.

(10) Patent No.: US 10,327,685 B2
(45) Date of Patent: Jun. 25, 2019

(54) SYSTEM AND METHOD FOR USING MULTIPLE SENSOR CALIBRATION METHODS

(71) Applicant: Becton, Dickinson and Company, Franklin Lakes, NJ (US)

(72) Inventors: Steven Keith, Madison, WI (US); Yongji Fu, Cary, NC (US); Elaine McVey, Durham, NC (US); Yiwen Zhang, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 933 days.

(21) Appl. No.: 14/134,881

(22) Filed: Dec. 19, 2013

(65) Prior Publication Data
US 2014/0180048 A1 Jun. 26, 2014

Related U.S. Application Data

(60) Provisional application No. 61/740,314, filed on Dec. 20, 2012.

(51) Int. Cl.
*A61B 5/1495* (2006.01)
*A61B 5/145* (2006.01)
(Continued)

(52) U.S. Cl.
CPC .......... *A61B 5/1495* (2013.01); *A61B 5/1486* (2013.01); *A61B 5/14532* (2013.01);
(Continued)

(58) Field of Classification Search
CPC . A61B 5/1495; A61B 5/14532; A61B 5/7225; A61B 5/1486; A61B 5/7282; A61B 5/746
See application file for complete search history.

(56) References Cited

U.S. PATENT DOCUMENTS 5,576,544 A * 11/1996 Rosenthal .......... A61B 5/14532
250/252.1
6,275,717 B1  8/2001 Gross et al.
(Continued)

OTHER PUBLICATIONS

Thomas et al. "A long-wavelength fluorescent glucose biosensor based on bioconjugates of galactose/glucose binding protein and Nile Red derivatives." Diabetes Technol Ther. Jun. 2006;8(3):261-8.*

(Continued)

*Primary Examiner* — Meredith Weare
(74) *Attorney, Agent, or Firm* — Dickinson Wright, PLLC

(57) ABSTRACT

The present invention relates to a system and method for improving glucose sensor accuracy by utilizing multiple calibration methods and selecting the most accurate method depending on a consensus glucose concentration estimate. Embodiments of the present invention comprise the steps of performing at least one in vivo update of surrounding glucose to acquire glucose values; calculating multiple updated calibration estimates using the updated glucose values; calculating an initial consensus glucose estimate from sensor output using each updated calibration estimate; applying a smooth crossover function to the multiple calibration estimates based on the value of the initial consensus glucose estimate; and adding weights to the multiple calibration estimates to acquire a consensus glucose estimate.

7 Claims, 7 Drawing Sheets

(51) Int. Cl.
*A61B 5/1486* (2006.01)
*A61B 5/00* (2006.01)
(52) U.S. Cl.
CPC .......... *A61B 5/7225* (2013.01); *A61B 5/7282* (2013.01); *A61B 5/746* (2013.01)

(56) References Cited

U.S. PATENT DOCUMENTS

| | | | | |
|---|---|---|---|---|
| 6,576,117 | B1* | 6/2003 | Iketaki | G01N 27/3274 204/400 |
| 7,496,392 | B2 | 2/2009 | Alarcon et al. | |
| 7,729,737 | B2* | 6/2010 | Ward | A61B 5/14532 600/316 |
| 7,787,923 | B2 | 8/2010 | Alarcon et al. | |
| 7,792,561 | B2 | 9/2010 | Alarcon et al. | |
| 8,579,816 | B2 | 11/2013 | Kamath et al. | |
| 2006/0281985 | A1* | 12/2006 | Ward | A61B 5/1486 600/365 |
| 2007/0135696 | A1* | 6/2007 | Ward | A61B 5/14532 600/345 |
| 2009/0036747 | A1* | 2/2009 | Hayter | A61B 5/01 600/300 |
| 2009/0076738 | A1* | 3/2009 | Kayihan | G01N 27/3273 702/25 |
| 2009/0101523 | A1* | 4/2009 | Deng | G01N 27/3273 205/777.5 |
| 2010/0312483 | A1 | 12/2010 | Peyser et al. | |
| 2011/0118571 | A1* | 5/2011 | Mandelis | A61B 5/14532 600/316 |
| 2011/0264378 | A1 | 10/2011 | Breton et al. | |

OTHER PUBLICATIONS

Dassau, et al. Real-Time hypoglycemia prediction suite using continuous glucose monitoring: a safety net for the artificial pancreas. Diabetes Care 2010, 33(6): 1249-54; Abstract, p. 1250, Fig 1 and its legend and col. 1 to p. 1251, col. 2.
Barcelo-Rico, et al. A multiple local models approach to accuracy improvement in continuous glucose monitoring. Diabetes Technol Ther. Jan. 2012, 14(1):74-82; Abstract, p. 75, 77.
Judge, et al. Continuous glucose monitoring using a novel glucose/galactose binding protein: results of a 12-hour feasibility study with the Becton Dickinson glucose/galactose binding protein sensor. Diabetes Technol Ther. 2011, 13(3):309-17; Abstract, p. 311, col. 2 to p. 312, col. 1.
Breton, et al. Optimum Subcutaneous Glucose Sampling and Fourier Analysis of Continuous Glucose Monitors. J Diabetes Sci Technol. 2008, 2(3): 495-500; Abstract, p. 498.
Stahl. Diabetes Mellitus Glucose Prediction by Linear and Bayesian Ensemble Modeling. PhD Thesis. Dec. 5, 2012 [The date is according to the document properties]. [retrieved from the Internet Feb. 10, 2014: <http://lup.lub.lu.se/luur/download?func=downloadFile&record0ld=3242077&fileOld=3242078>]; p. 86-91,112.
Girardin, et al. Continuous glucose monitoring: a review of biochemical perspectives and clinical use in type 1 diabetes. Clin Biochem. 2009, 42(3):136-42; Abstract. p. 139, Fig 2 and its legend; p. 140, col. 2 to p. 141, col. 2.
Bequette. Continuous glucose monitoring: real-time algorithms for calibration, filtering, and alarms. J Diabetes Sci Technol. 2010, 4(2):404-18; in entirety.
Rossetti, et al. Estimating plasma glucose from interstitial glucose: the issue of calibration algorithms in commercial continuous glucose monitoring devices. Sensors (Basel) 2010, 10(12):10936-52; Abstract, p. 10938-10945.
Davey, et al. Contribution of an intrinsic lag of continuous glucose monitoring systems to differences in measured and actual glucose concentrations changing at variable rates in vitro. J Diabetes Sci Technol. 2010, 4(6):1393-9; p. 1397, Fig 2 and its legend.
Boyne, et al. Timing of changes in interstitial and venous blood glucose measured with a continuous subcutaneous glucose sensor. Diabetes 2003, 52(11 ):2790-4: Abstract, p. 2791, col. 1.

* cited by examiner

SYSTEM AND METHOD FOR USING MULTIPLE SENSOR CALIBRATION METHODS

This application claims the benefit under 35 U.S.C. § 119(e) of U.S. provisional application No. 61/740,314, filed Dec. 20, 2012, the entire contents of which are hereby incorporated by reference.

BACKGROUND OF THE INVENTION

Field of the Invention

The present invention relates to a system and method for improving glucose sensor accuracy by utilizing multiple calibration methods and selecting the most accurate method depending on a consensus glucose concentration estimate.

Description of the Related Art

Monitoring in vivo concentrations of physiologically relevant compounds to improve diagnosis and treatment of various diseases and disorders is a desirable goal and would enhance the lives of many individuals. Advances in this area show particular promise in the area of facilitating adequate metabolic control in diabetics.

The use of glucose sensors in the medical field is widespread. The regular monitoring of blood glucose levels of diabetic patients at home as well as the use of glucose monitoring in intensive care units are two primary examples. The usual aim in developing a glucose sensor is to produce a digital electronic signal, which is proportional to the glucose concentration.

Most conventional electrochemical glucose sensors (glucose-oxidase or GOx based) employ a linear calibration method whereby sensor accuracy will degrade as glucose levels move further from an in vivo update point.

For example, a glucose oxidase (GOx) sensor output relative to the surrounding glucose can expressed as a straight line:

$$S = m*\text{glucose} + b \quad (1)$$

or equivalently $$\text{Glucose} = (S-b)/m, \quad (2)$$

where
S=sensor output,
m=sensor sensitivity, and
b=sensor bias

An in vivo calibration update, where a known plasma glucose value is used to correct the calibration equation, can be used to correct the estimate of either m or b. GOx sensors are typically updated by changing the slope term m.

Algebraically, a single pair of sensor outputs and glucose values can only be used to change one parameter at a time in equation (2). It is also possible to use a priori information to generate a correction for both terms. The a priori information would contain known relationships between m and b using algorithms such as a Bayesian approach, Kalman filters, or the like.

In either case, a change to the parameters of a linear equation does not change the shape of the resulting line, only its intercept and/or its slope. Because the calibration equation is a straight line, the magnitude of sensor errors increases as the distance from the calibration point increases. If, for example, the GOx sensor is calibrated in the normal glucose range, errors will tend to be larger in the hypoglycemic and hyperglycemic ranges.

Accordingly, there exists a need to improve upon the increased sensor error caused by the use of a single linear calibration equation as the distance from the calibration point increases.

Additionally, there is a need for a system and method for improving glucose sensor accuracy by utilizing a curvilinear calibration equation that takes advantage of a multiplicity of parameters so that accuracy can be optimized in all glucose regions, instead of only in the glucose region near the calibration point.

Moreover, there is a need for a system and method for improving glucose sensor accuracy by utilizing several calibration methods whereby the changing shape of a calibration curve allows the distribution of sensor error to be changed because the relationship between the error and the glucose levels is no longer necessarily fixed.

Furthermore, there is also a need for a system and method for improving glucose sensor accuracy by utilizing several calibration methods and selecting the most accurate method depending on a consensus glucose concentration estimate.

SUMMARY OF THE INVENTION

An object of the present invention is to substantially address the above and other concerns, and provide a system and method for improving glucose sensor accuracy by utilizing multiple calibration methods and selecting the most accurate method depending on a consensus glucose concentration estimate.

Another object of embodiments of the present invention is to provide improved glucose sensor accuracy by performing at least one in vivo update of surrounding glucose to acquire glucose values; calculating multiple updated calibration estimates using the updated glucose values; calculating an initial consensus glucose estimate from sensor output using each updated calibration estimate; applying a smooth crossover function to the multiple calibration estimates based on the value of the initial consensus glucose estimate; and adding weights to the multiple calibration estimates to acquire a consensus glucose estimate.

BRIEF DESCRIPTION OF THE DRAWING FIGURES

The various objects, advantages and novel features of the exemplary embodiments of the present invention will be more readily appreciated from the following detailed description when read in conjunction with the appended drawings, in which.

Throughout the drawing figures, like reference numbers will be understood to refer to like elements, features and structures.

DETAILED DESCRIPTION OF EXEMPLARY EMBODIMENTS

Figure 1:
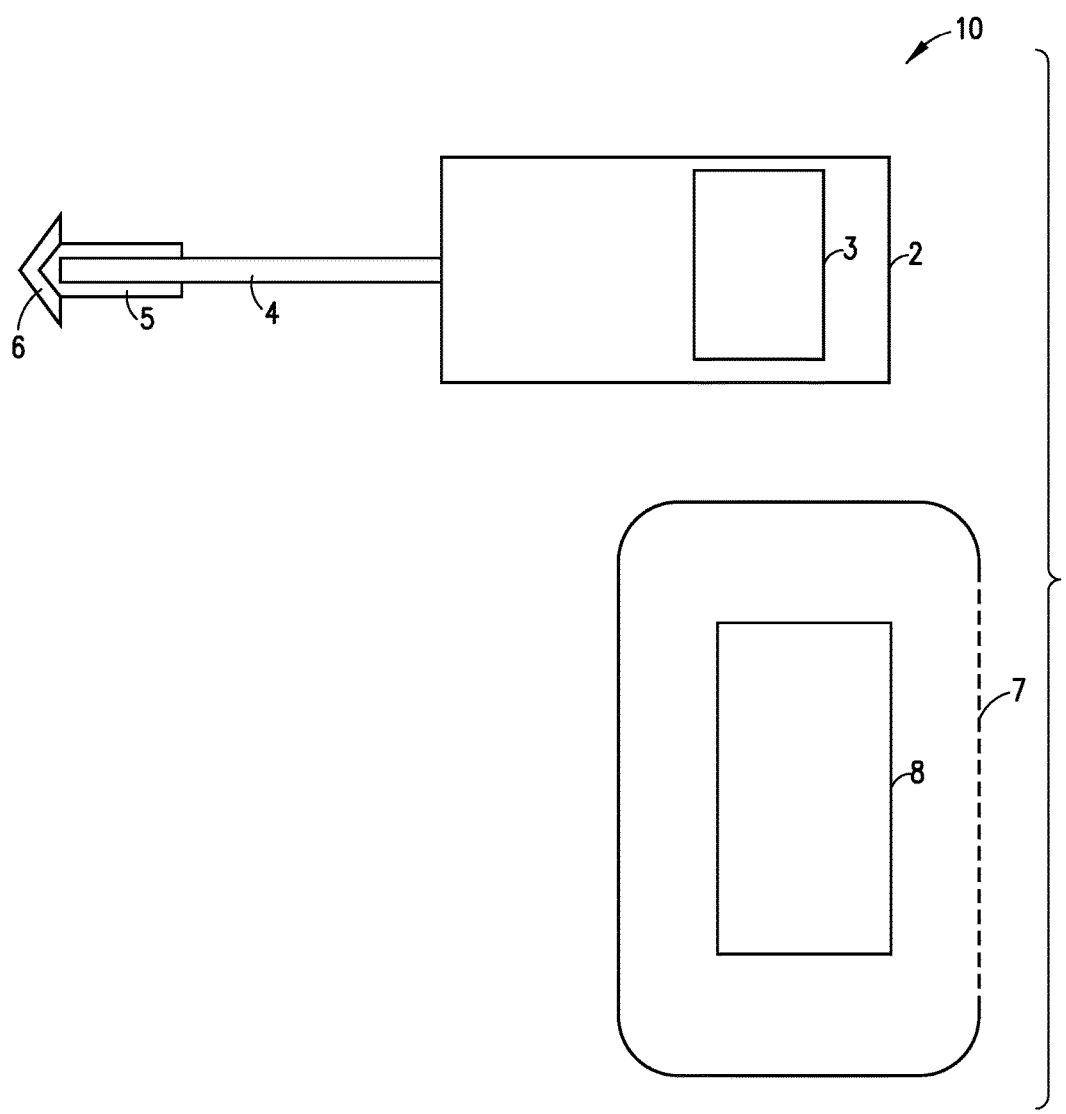
FIG. 1 depicts an illustrative embodiment of the basic components of a glucose sensor calibration system of the present invention.

The matters defined in the description are provided to assist in a comprehensive understanding of the embodiments of the invention and are merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

Embodiments of the present invention seek to overcome the disadvantages of an increased sensor error caused by the use of a single linear calibration equation in conventional enzyme-sensing glucose oxidase (GOx) sensors as the distance from the single calibration point increases.

The calibration equation for a glucose binding protein (GBP) based sensor of illustrative embodiments of the present invention is very different from that of a contemporary GOx sensor. When a fluorescent label is attached to GBP, the relationship between sensor output and the surrounding glucose can be expressed as:

$$S=(S0+Sinf*Glucose/KD)/(1+Glucose/KD) \quad (3)$$

or $$Glucose=KD*(S-S0)/(Sinf-S), \quad (4)$$

where
S=sensor output,
KD=apparent binding constant,
S0=sensor output when no glucose is present, and
Sinf=sensor output when glucose is present at saturating levels.

There is a further relationship between continuous glucose sensor outputs and plasma glucose, which is recognized, but not always utilized. Continuous glucose sensors located in the dermis measure glucose concentration in the interstitial fluid (ISF), not plasma. The two glucose levels (ISF and plasma) can be related by a diffusion-based transport equation:

$$PG=DF*\{ISFG+Tau*d(ISFG)/dt\}, \quad (5)$$

where
PG=plasma glucose concentration,
ISFG=interstitial glucose concentration,
DF=in vivo dilution factor,
Tau=in vivo time constant, and
d(ISFG)/dt=the time rate of change of the interstitial glucose.

Combining these two equations, we have an expression for plasma glucose:

$$PG=DF*\{KD*(S-S0)/(Sinf-S)+Tau*d[KD*(S-S0)/(Sinf-S)]/dt\} \quad (6)$$

In the case of a GBP sensor, an in vivo update can be used to correct any of the three parameters of the binding equation (S0, Sinf, KD) or either parameter of the plasma-ISF relationship (DF, Tau). Unlike with a single linear calibration equation, changes to different parameters can change the shape of the calibration curve as well as the intercept of the curve. The changing shape of the calibration curve allows the distribution of sensor error to be changed because the relationship between the error and glucose levels is no longer necessarily fixed.

Not all parameters have different effects on the sensor-glucose relationship. In the case where neither changes over time, DF and KD for example, are always combined in equation (6), so changes in either value will have the same impact on the shape of the calibration curve.

During an in vivo update, a set of updated values for each parameter in equation (6) can be calculated, in effect constructing a family of calibration curves, each having a different error distribution relative to glucose levels. Accordingly, a curve which is the most accurate in any given glucose region may be determined. Therefore, an initial estimate of glucose can be used to determine which calibration curve to apply, and thereby attain the most accurate estimate available.

Illustrative embodiments of the present invention provide a system and method for improving glucose sensor accuracy by utilizing several calibration methods and selecting the most accurate method depending on a consensus glucose concentration estimate. Embodiments of the present invention may be used with any type of known GBP sensor.

An illustrative preferred embodiment of the components of a glucose sensor calibration system 10 of the present invention is shown in FIG. 1. The glucose sensor calibration system 10 includes a combination of elements, including but not limited to, electromagnetic energy emitters, electromagnetic energy detectors, various mirrors, filters, electronics, holographic optics, dichroic elements, and optical standards needed to send interrogating radiation from the electromagnetic energy emitter down an optical conduit 4 to a sensing element 6 and then to resolve and interpret the return luminescent signal. The return luminescent signal from the reporter group changes in response to changing concentrations of the analyte to be detected.

An optical system 2 may comprise a computer or microprocessor 3 which handles signal processing, mathematical manipulation of one or more signals, and data storage and handling. The computer or microprocessor 3 may be in physical contact with the other components of the optical system 2 or, in a preferred embodiment, may be physically separated by up to several meters from the other components optical system.

In this embodiment, information from the electromagnetic energy detectors and electronic processing elements in the glucose sensor calibration system 10 is communicated wirelessly to the computer or microprocessor 3. The computer or microprocessor 3 may also store calibration information specific to the sensing element 6.

Light of one or more wavelengths produced in an optical system 2 is channeled down an optical conduit 4 to the sensing element 6. Optical conduit 4 may be either an optical fiber or a short light guide that transmits light with minimal loss.

The sensing element 6 consists of one or more binding proteins with one or more associated luminescent reporter groups either immobilized in a polymeric matrix, attached to a polymer chain, incorporated in a disposable tip 5, attached directly to the distal end of the optical conduit 4, or attached to a connector. The sensing element 6 can also consist of additional luminescent reference groups that are optionally attached to biomolecules, polymers, or organic molecules for the purpose of providing a reference or calibration signal. Sensing element 6 can be attached to the distal end of optical conduit 4, either directly or via a polymer matrix, or, in the preferred embodiment, attached to a disposable tip 5 that is attached to the distal end of the optical conduit 4. In this case, the disposable tip 5 is positioned against optical conduit 4 either mechanically, via adhesive, or by any other suitable means known to those of skill in the art.

The glucose sensor calibration system 10 may also comprise a wireless glucose blood measurement device 7 to obtain the in vivo calibration measurement. The glucose blood measurement device can have a display 8 which presents glucose related information to the user. Alternatively, manual entry of the blood glucose value into the glucose blood measurement device 7 can be implemented. U.S. Pat. Nos. 7,496,392; 7,787,923; and 7,792,561, which are incorporated by reference herein, disclose exemplary glucose sensors which may be used in the practice of the present invention.

Figure 2:
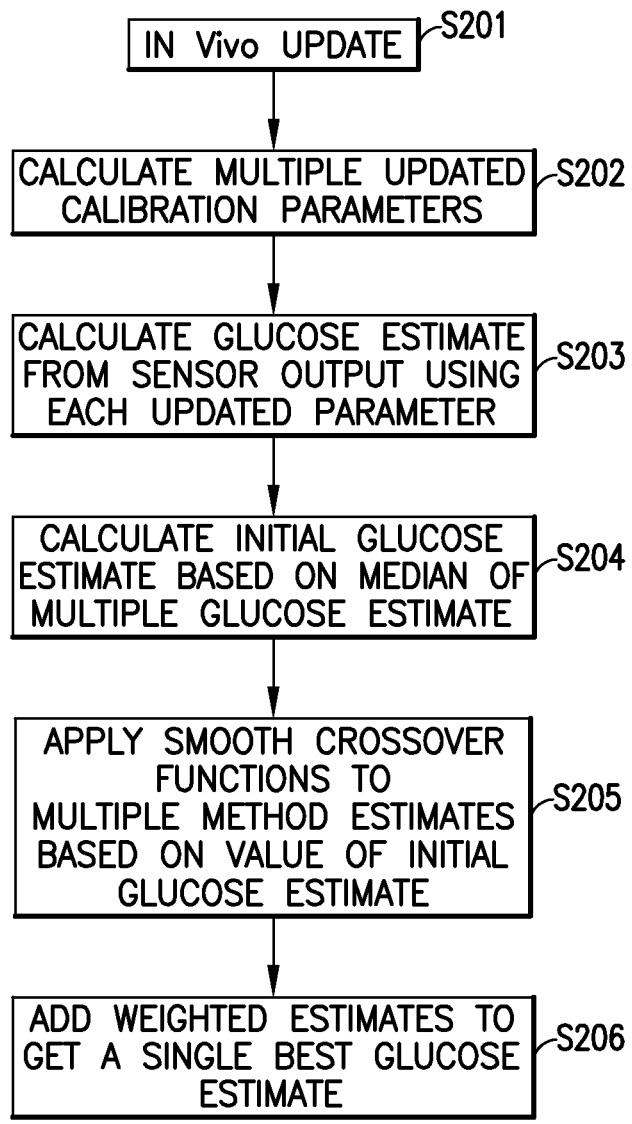
FIG. 2 depicts a flow chart of an illustrative method of the present invention for improving glucose sensor accuracy by utilizing several calibration methods.

A flow chart illustrating a method of the present invention for improving glucose sensor accuracy by utilizing several calibration methods is shown in FIG. 2.

Researchers applied several different calibration methods to a set of clinical data. For three glucose regions (hypoglycemic: glucose<75 mg/dL, hyperglycemic: glucose>180 mg/dL, and normal (between 75 and 180 mg/dL), three different calibration update methods were found to provide the best accuracy as measured by median absolute relative difference (medARD, ARD=absolute value of sensor error divided by actual glucose) in each glucose region. Importantly, none of these three methods provided the best accuracy in all three glucose regions.

The illustrative glucose sensor calibration method of the present invention accounts for the fact that different calibration methods yield the best accuracy in different glucose regions.

In embodiments of the present invention, at least one in vivo update is performed using a blood sample to measure the plasma glucose level value, as described in step S201 of FIG. 2. The updated glucose value is then used to calculate several updated calibration parameters, as described in step S202.

In step S203, each updated parameter is used to calculate sensor glucose estimates from the sensor outputs using three different calibration methods. The details of the different calibration methods are described with reference to FIGS. 3-7.

An illustrative embodiment of the present invention refer to calibration methods 1-3, being respectively best in the low, medium, and high glucose regions (hypoglycemic: glucose<75 mg/dL, hyperglycemic: glucose>180 mg/dL, and normal: between 75 and 180 mg/dL). Each method has a different overall error distribution relative to glucose levels.

Figure 3:
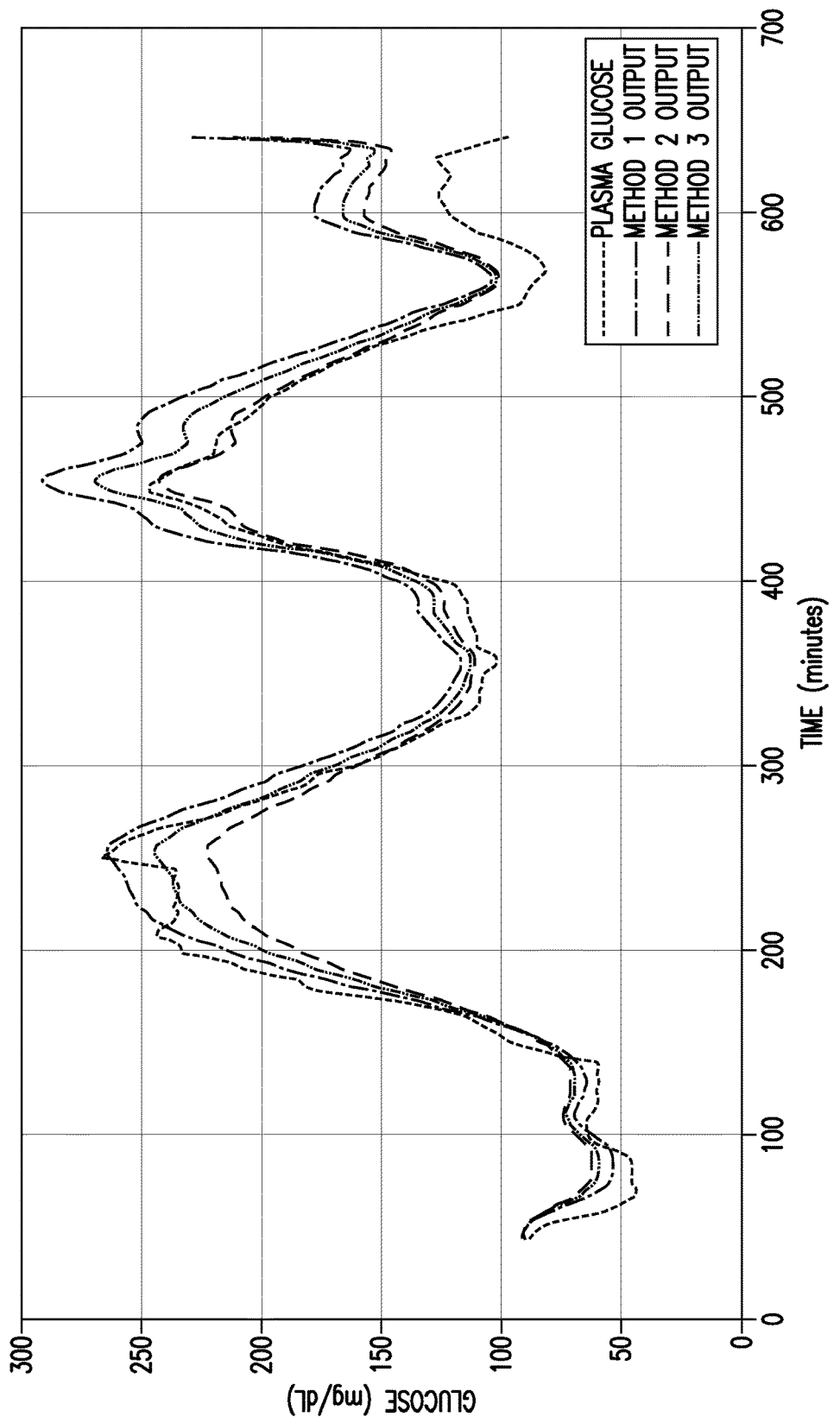
FIG. 3 depicts an illustrative example of sensor glucose estimates using three different calibration methods of embodiments of the present invention.

For the sensor glucose estimates illustrated in FIG. 3, each calibration method provides different glucose estimates. These three methods have their own best accuracy in the low, medium, and high glucose levels when compared on a group of sensors.

Figure 4:
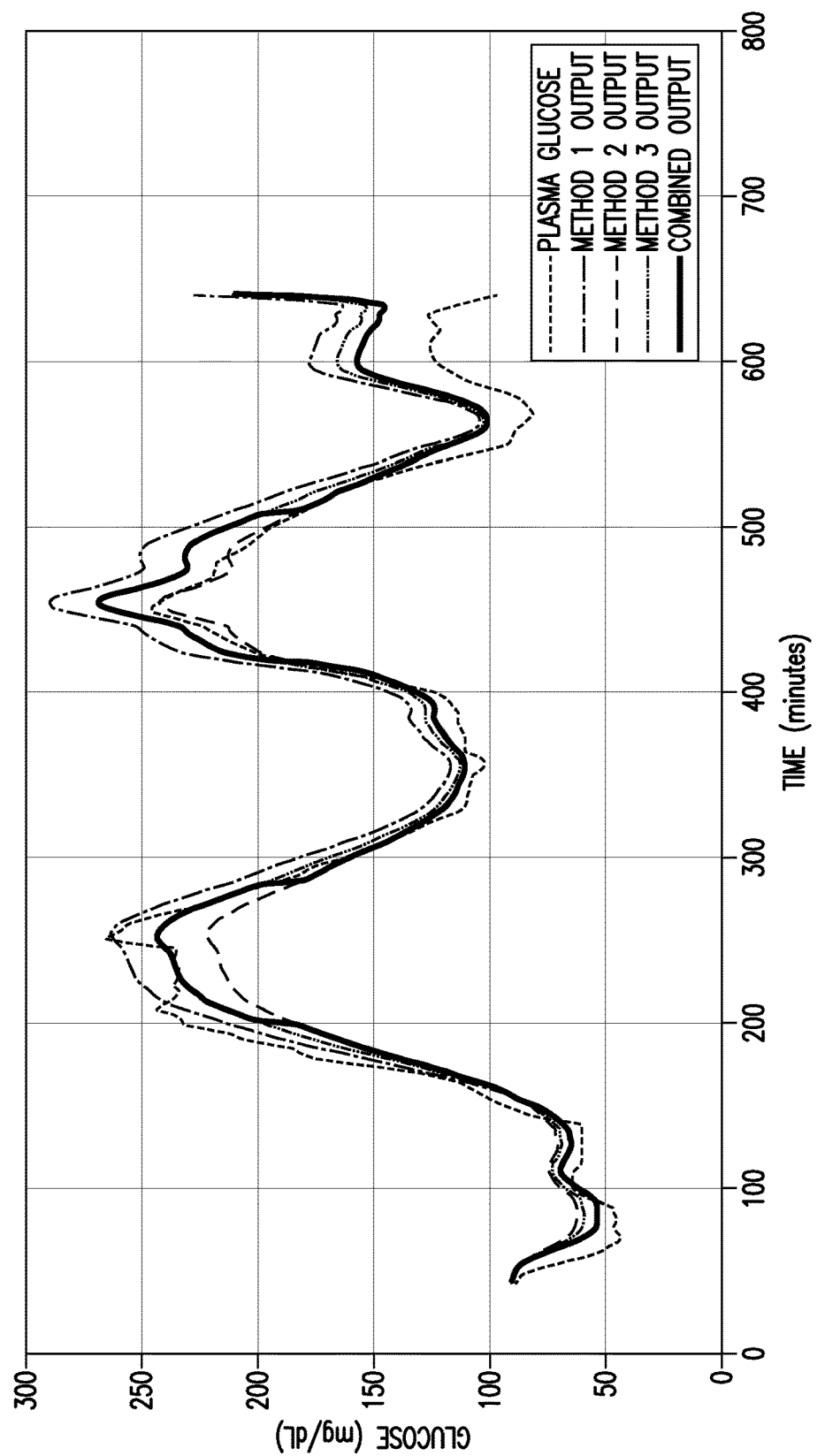
FIG. 4 depicts an illustrative example of a consensus glucose concentration estimate of embodiments of the present invention.

Using the sensor outputs acquired from step S203, the median of all three estimates is used to calculate an initial consensus glucose estimate, as described in step S204. The median value is used to select the appropriate calibration method depending on the determined glucose level. For example, the initial consensus glucose estimate tracks closely to method 1 in the low glucose region, method 2 in the normal region, and method 3 in the high glucose region, as shown in FIG. 4.

Figure 5:
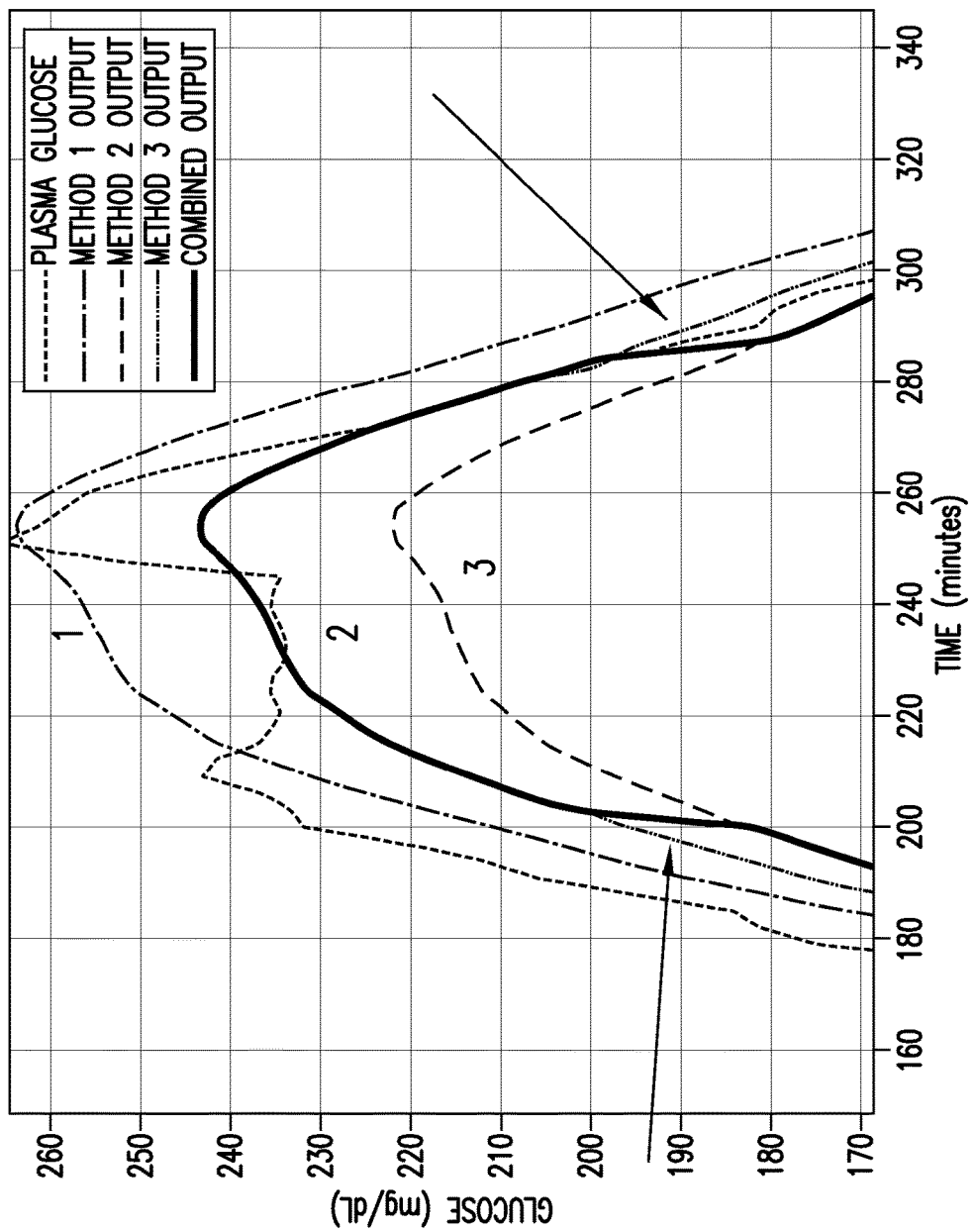
FIG. 5 depicts an illustrative example of a sharp jump in an output of an initial consensus glucose concentration estimate.

As illustrated in FIG. 5, a sharp jump in the output of the consensus glucose concentration estimate occurs as glucose levels cross the boundary between the normal and high glucose levels. The combined calibration method uses method 2 in the normal region and method 3 in the high region. The arrows shown in FIG. 5 indicate the transition events.

To avoid the sharp and instantaneous jump illustrated in FIG. 5, embodiments of the present invention apply a crossover weighting function to the multiple method estimates based on the value of the initial consensus glucose estimate, as described in step S205.

Figure 6:
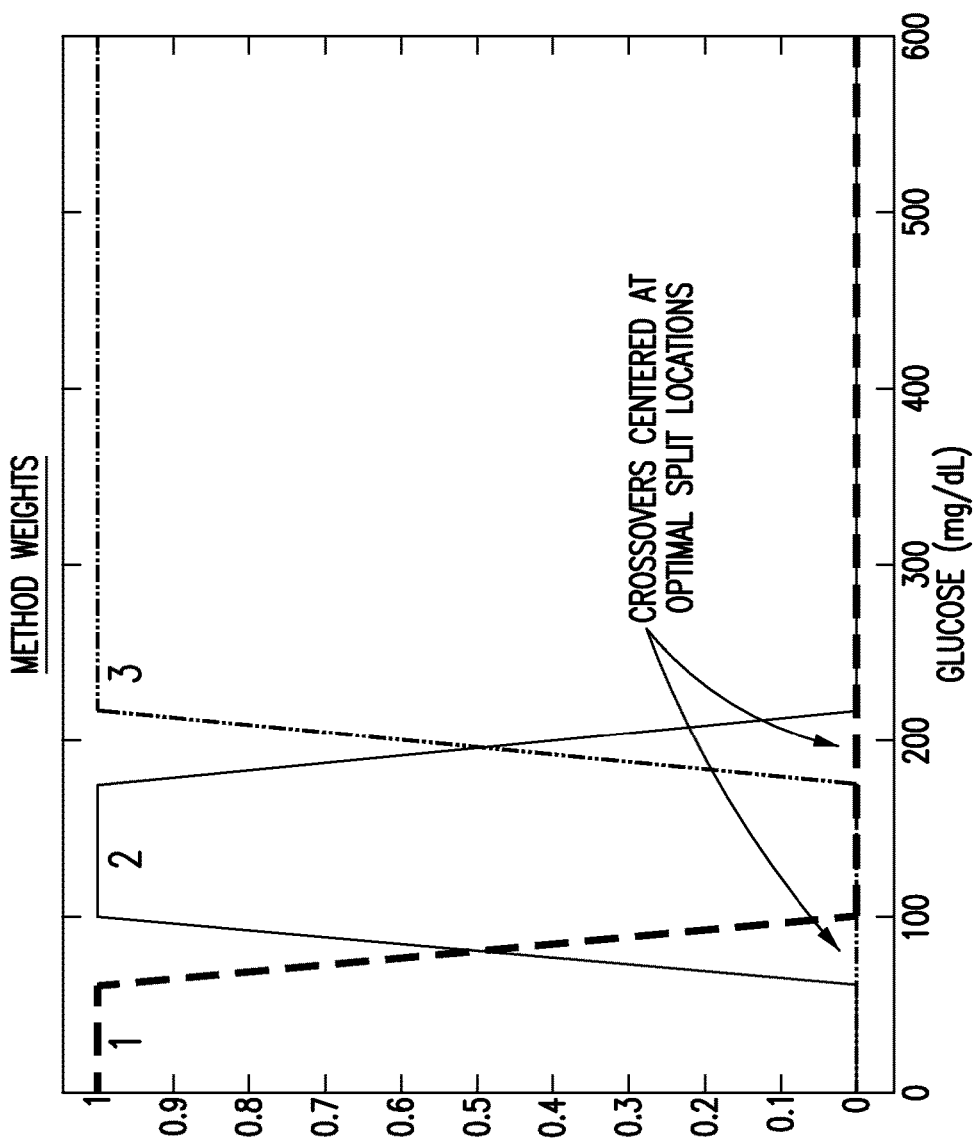
FIG. 6 depicts an illustrative example of the crossover weighting function of embodiments of the present invention.

FIG. 6 illustrates an example of the crossover weighting function of embodiments of the present invention. The crossover weighting function is applied to the output of each method so that at any glucose level the combined weight of the three calibration methods is equal to one.

As illustrated in FIG. 6, the best calibration method is fully weighted in each respective glucose region. At boundaries between levels, the weights for each method are changed such that the total weight is always equal to one, as described in step S206. Accordingly, after applying the crossover weighting function to the output of each method, the two neighboring weights transition from one to zero (or vice versa) such that the total weight is always equal to one.

The resulting glucose output now transitions smoothly across the glucose level boundaries. The crossover weighting function also serves to reduce the chance that the initial consensus glucose estimate will result in "jitter" between two adjacent readings, and eliminate the situation where an initial consensus glucose estimate and the "best" estimate might lie in different regions.

Figure 7:
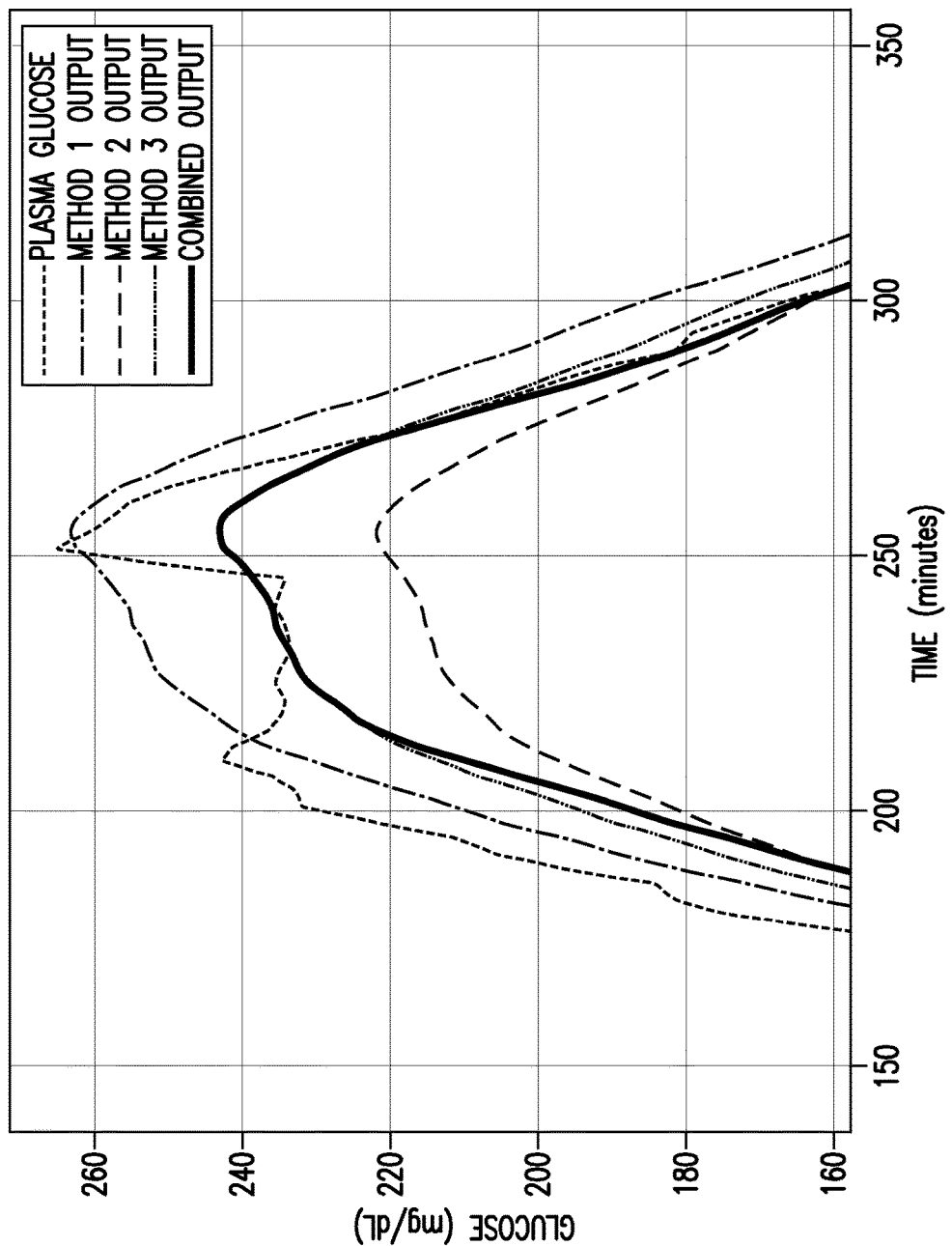
FIG. 7 depicts an illustrative example of a smooth transition between different calibration methods after applying the crossover weighting function of embodiments of the present invention.

The resulting glucose estimate during a period of transition into and out of the hyperglycemic region is shown in FIG. 7. Note that there is no longer a sharp "jump" in glucose values at the boundary.

Further, the calibration methods can be selected by a comparative analysis of a representative set of in vivo data and the crossover functions can be determined by an optimization of the final best estimates according to the intended use of the estimates.

For example, as shown in the referenced technical report, raw sensor outputs and reference glucose values were collected for a number of subjects in the course of a clinical trial. Various in vivo calibration methods were applied to the sensor outputs to obtain multiple sets of glucose estimates. Estimates were compared to the reference glucose values to produce several accuracy metrics, such as mean and median absolute percent error, correlation coefficient, percentage of points located in Clarke Error Grid ranges. [Clarke Error Grid is well known to those well versed in the field: it represents graphically the increasing risk to a patient due to increasing errors in a sensor's glucose estimate. Depending on the actual glucose value, sensor errors of similar magnitude could result in a clinical treatment decision with patient risk ranging from none (accurate sensor readings leading to proper treatment) to serious (erroneous sensor readings leading to erroneous treatment with considerable risk to patient's health).] Accuracy metrics are used to assess the utility of different calibration methods overall, and for specified glucose ranges. As will be described, different glucose ranges may be considered depending on the desired application or use of the sensor glucose estimates.

Methods for optimizing a set of parameters for a numerical process are well known to those well versed in the field. A common method is to create a mathematical simulation of the process being investigated, vary the inputs to the simulation in a particular manner, and examine the outputs of the simulation. A common method is often referred to as "Monte Carlo" simulation, wherein inputs are randomly varied, or varied with a predetermined distribution of probabilities. The chosen distribution will reflect the understanding of the processes involved in the particular process. For example, a BGP glucose sensor could be simulated using normally distributed values for the calibration parameters contained in equation (4). This could reflect the situation where sensors were being manufactured according to a process which resulted in a normal distribution of sensor characteristics. A suitable simulation would allow the impact of the variation in sensor characteristics to result in variation in one or more outputs, for example, in the accuracy of a sensor's glucose estimates. The sensor outputs could be further used in a simulation representing for example a feedback control system with the objective of maintaining a stable glucose level in a diabetic patient. The impact of changes to parameters relating to the calibration process, for example the location of the weighting function crossover points, on the outputs of the simulation, for example the stability of a control system, could be thus measured. The input parameters can be varied until the simulation outputs achieve the best possible or "optimum" values.

The calibration method of embodiments of the present invention can be applied iteratively. For example, after the consensus glucose estimate is calculated, the consensus glucose estimate is used to recalculate the weights, and the glucose level is re-estimated. In effect, when glucose is within the transition window between two glucose regions, the calibration method associated with the region furthest from this boundary can be ignored, as the estimate from that calibration method is the least accurate of the available calibration estimates.

For the data set examined in the above examples, accuracy for each calibration method and the consensus glucose estimate are shown in Table 1. As shown in Table 1, the consensus glucose calibration estimate accuracy is nearly as accurate as the best calibration method in the low and medium glucose regions, and slightly better than the best single calibration method in the high glucose region. Overall, the consensus glucose calibration estimate is superior to any single calibration method.

TABLE 1

Accuracy results for individual methods and combined method. Accuracy reported as median Absolute Relative Difference (medARD).

| method | Low glucose | Medium glucose | High glucose | overall |
| --- | --- | --- | --- | --- |
| 1 | 9.5 | 10.8 | 8.5 | 9.8 |
| 2 | 8.0 | 13.3 | 10.4 | 11.7 |
| 3 | 11.4 | 8.9 | 10.2 | 9.5 |
| combined | 8.2 | 9.1 | 8.4 | 8.7 |

For the above example, the glucose region boundaries were set at 82 and 196 mg/dL, and the transition window was set to 40 mg/dL. These values can be optimized according to different criteria as described in embodiments of the present invention below.

In preferred embodiments of the present invention the settings for a calibration method voting scheme are to split the low, medium, and high glucose regions at 82 and 196 mg/dL, with a transition window of 20 mg/dL above and below each split point. Alternatively, the low-medium split can be set between about 75 and 90 mg/dL. Likewise, the medium-high split can be set between about 180 and 210 mg/dL. The transition windows can be reduced to about 5 mg/dL on either side of the split points.

However, glucose boundaries can be variously set according to the final use of the glucose estimates according to other embodiments of the present invention.

In an embodiment of a nocturnal hypoglycemia alarm of the present invention, accuracy is most critical in the approach to hypoglycemia, in the region of approximately 70 to 110 mg/dL. In this use, it is important that the true glucose rate of change not be altered by the calibration method selection so that the boundary between low and normal glucose regions would be chosen to be outside these critical regions. During calibration methods optimization, accuracy in the specific glucose region can be selected. In the case of a dedicated alarm, it may be possible that optimal results are achieved with a single calibration method which provides the best accuracy in the specifically desired region. The comparative methods analysis can be tailored to use this region as a specific metric.

In an embodiment of the present invention with a closed loop, the control of insulin using classical and modern control theory is in part driven by the glucose rate of change. It is critical in this application to provide smooth transitions between glucose regions, so wider transition windows may be favored.

In a control-to-range version of a closed loop of embodiments of the present invention, the goal is to keep glucose within a specified range of approximately 80-140 mg/dL. Therefore, it is important to provide the smoothest sensor output in this region, so that method selection boundaries could be set outside these boundaries.

Additionally, in cases where calculations are expensive, or memory is limited, the calibration methods can be reduced to two, and a single glucose boundary can be utilized. The applications mentioned above, such as the hypoglycemia alarm, could be achieved using only two glucose regions, thus avoiding the need to make real-time decisions.

Furthermore, the crossover weighting function shapes of embodiments of the present invention can be varied and the continuously smooth transition can be based on different filter designs (e.g. Butterworth).

Accordingly, illustrative embodiments of the present invention overcome the increased sensor error caused by use of a single linear calibration equation and the use of an in vivo update point to adjust the slope or bias term. By taking advantage of the multiplicity of parameters in the GBP calibration equation, accuracy can be optimized in all glucose regions, instead of only in the glucose region near the in vivo update point.

Moreover, illustrative embodiments of the present invention provide a GBP sensor calibration equation which is curvilinear, wherein changes to different parameters have different effects on the shape of the resulting curve. Hence, the calibration curve can be defined in multiple ways using a single in vivo update point, maximizing the resulting accuracy in different glucose regions.

Illustrative embodiments of the present invention provide a system and method for improving glucose sensor accuracy by utilizing multiple calibration methods and selecting the most accurate method depending on a consensus glucose concentration estimate.

While certain exemplary embodiments of the present invention have been shown and described herein with reference to certain preferred embodiments thereof, it will be understood by those skilled in the art that various changes in form and details may be made therein without departing from the spirit and scope of the invention.

What is claimed is:

1. A method for improving glucose sensor accuracy by utilizing multiple calibration estimates, the method comprising the steps of:
    performing at least one in vivo update of surrounding glucose to acquire glucose values with the glucose sensor;
    applying multiple calibration estimates to the updated glucose values;
    calculating multiple updated calibration estimates using the updated glucose values; wherein each of the multiple calibration estimates is more accurate than the other of the multiple calibration estimates within one of a plurality of glucose concentration ranges;
    calculating an initial consensus glucose estimate value from sensor output using each updated calibration estimate;
    weighting the multiple updated calibration estimates based on the value of the initial consensus glucose estimate value such that the weights sum to unity, wherein the weights are smoothly shifted from zero to one among the multiple calibration estimates as a function of the initial consensus glucose estimate value in glucose concentration regions around boundaries of the plurality of glucose concentration ranges;
    determining a glucose level with the glucose sensor based on a weighted multiple calibration estimates; and
    displaying the determined glucose level on a display of a glucose blood measurement device.

2. The method of claim 1, wherein the initial consensus glucose estimate is calculated by calculating a median of the multiple updated calibration estimates.

3. The method of claim 1, further comprising determining a calibration estimate by comparative analysis of a representative set of in vivo data.

4. The method of claim 1, further comprising setting a nocturnal hypoglycemia alarm in a glucose region between 70 to 110 mg/dL.

5. The method of claim 1, wherein the multiple updated calibration estimates are calculated based on the equation:

$$S=(S0+Sinf*Glucose/KD)/(1+Glucose/KD) \text{ or}$$

$$Glucose=KD*(S-S0)/(Sinf-S), \text{ where}$$

S=sensor output,
KD=apparent binding constant,
S0=sensor output when no glucose is present, and
Sinf=sensor output when glucose is present at saturating levels.

6. The method of claim 5, wherein glucose level is determined based on a diffusion-based transport equation:

$$PG=DF*\{ISFG+Tau*d(ISFG)/dt\}, \text{ where}$$

PG=plasma glucose concentration,
ISFG=interstitial glucose concentration,
DF=in vivo dilution factor,
Tau=in vivo time constant, and
d(ISFG)/dt=the time rate of change of the interstitial glucose.

7. The method of claim 6, wherein glucose level is determined based on an equation for plasma glucose expressed as:

$$PG=DF*\{KD*(S-S0)/(Sinf-S)+Tau*d[KD*(S-S0)/(Sinf-S)]/dt\}.$$

* * * * *